(12) United States Patent
Tarui

(10) Patent No.: US 8,178,044 B2
(45) Date of Patent: May 15, 2012

(54) LIQUID PROPERTY DETECTING DEVICE

(75) Inventor: Jun Tarui, Kariya (JP)

(73) Assignee: Denso Corporation, Kariya (JP)

( * ) Notice: Subject to any disclaimer, the term of this patent is extended or adjusted under 35 U.S.C. 154(b) by 90 days.

(21) Appl. No.: 12/607,398

(22) Filed: Oct. 28, 2009

(65) Prior Publication Data

US 2010/0108507 A1    May 6, 2010

(30) Foreign Application Priority Data

Oct. 31, 2008 (JP) ................................. 2008-280826
Sep. 16, 2009 (JP) ................................. 2009-214796

(51) Int. Cl.
*G01N 15/06* (2006.01)
*G01N 33/00* (2006.01)
*G01N 33/48* (2006.01)

(52) U.S. Cl. ... 422/68.1; 422/50; 422/82.01; 422/82.02; 436/43; 436/149

(58) Field of Classification Search ............ 422/50, 422/68.1, 82.01, 82.02; 436/43, 149
See application file for complete search history.

(56) References Cited

U.S. PATENT DOCUMENTS

| 5,260,663 | A  | * | 11/1993 | Blades ........................... 324/442 |
| 5,270,663 | A  | * | 12/1993 | Sano et al. ..................... 324/676 |
| 7,659,731 | B2 | * | 2/2010  | Lin et al. ........................ 324/693 |
| 2008/0053202 | A1 | * | 3/2008 | Rohklin et al. ............... 73/61.41 |
| 2008/0197863 | A1 | * | 8/2008 | Lin et al. ....................... 324/693 |
| 2009/0251126 | A1 | * | 10/2009 | Ishino et al. ................. 324/71.1 |

FOREIGN PATENT DOCUMENTS

| JP | 4-75957 | 7/1992 |
| JP | 6-3313 | 1/1994 |

* cited by examiner

*Primary Examiner* — Brian J Sines
(74) *Attorney, Agent, or Firm* — Nixon & Vanderhye P.C.

(57) ABSTRACT

A liquid property detecting device includes a switch portion switching an electrode to charge with a standard voltage generated by a generator, or discharge through a grounding. An operation signal output portion outputs an operation signal to the switch portion so as to switch in a predetermined switch period. A voltage of the electrode is output as a detection signal, when the standard voltage is applied to the electrode. A signal process portion calculates liquid property based on the detection signals. A gain of the signal process portion relative to the detection signal is increased, as the detection signal is decreased.

3 Claims, 12 Drawing Sheets

ETHANOL CONCENTRATION

| Vb | f1 (kHz) | f2 (kHz) | Δf (kHz) |
|---|---|---|---|
| 0<Vb<P | 500 | 100 | 400 |
| P≦Vb<Q | 500 | 300 | 200 |
| Q≦Vb | 500 | 400 | 100 |

| Vb | E |
|---|---|
| $0 < Vb < P$ | E1 |
| $P \leq Vb < Q$ | E2 |
| $Q \leq Vb$ | E3 |

| $V_{bN}$ | I ($0 < V_{bN} \leq \varepsilon$) | II ($\varepsilon < V_{bN} \leq \phi$) | III ($\phi < V_{bN}$) |
|---|---|---|---|
| $\Delta f$ | H (H>J) | J | K (J>K) |

| $V_{b100}$ | I ($0 < V_{b100} \leq \varepsilon$) | II ($\varepsilon < V_{b100} \leq \phi$) | III ($\phi < V_{b100}$) |
|---|---|---|---|
| GAIN | $\gamma$ ($\gamma > \beta$) | $\beta$ | $\alpha$ ($\beta > \alpha$) |

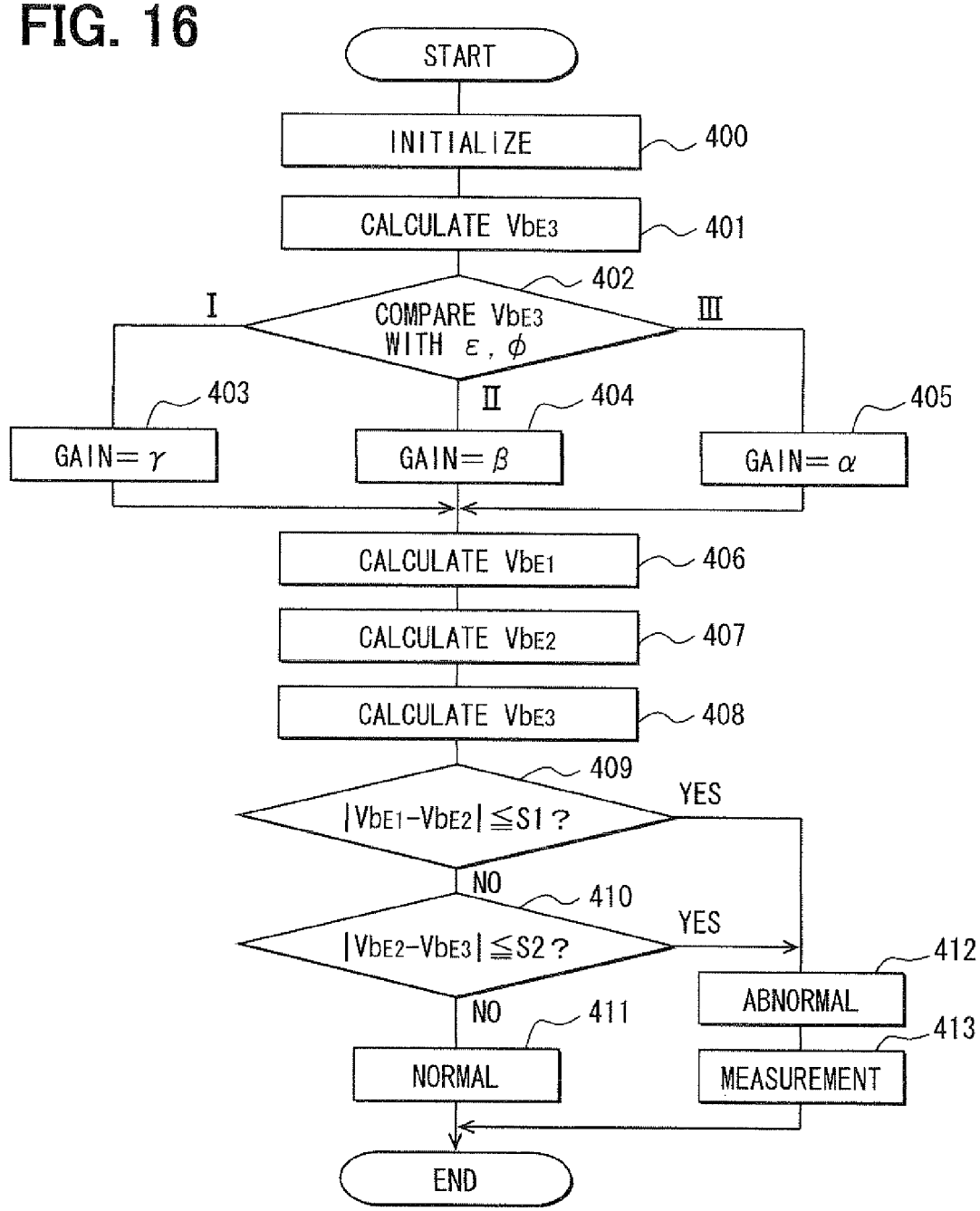

LIQUID PROPERTY DETECTING DEVICE

CROSS REFERENCE TO RELATED APPLICATION

This application is based on Japanese Patent Application No. 2008-280826 filed on Oct. 31, 2008 and Japanese Patent Application No. 2009-214796 filed on Sep. 16, 2009, the disclosures of which are incorporated herein by reference in their entirety.

BACKGROUND OF THE INVENTION

1. Field of the Invention

The present invention relates to a liquid property detecting device.

2. Description of Related Art

A liquid property detecting device detects a concentration of a component included in liquid. For example, an ethanol concentration is detected in a mixed liquid in which gasoline and ethanol are mixed, when the mixed liquid is used as a fuel for a vehicle engine. When ethanol is used for the vehicle engine, exhaust gas emitted from the vehicle engine has less toxic component, compared with a typical engine using only gasoline.

However, a suitable air-fuel ratio is different between the mixed liquid and gasoline. The vehicle engine is required to have the suitable air-fuel ratio so as to provide higher heat efficiency and to reduce the toxic component included in exhaust gas. Therefore, when the mixed liquid is used for the vehicle engine, an amount of ethanol included in the mixed liquid is measured. The measurement of ethanol concentration is important.

JP-A-6-3313 discloses a liquid property detecting device to detect an ethanol concentration in a mixed liquid in which gasoline and ethanol are mixed. The liquid property detecting device has a nonconductive tube and electrodes arranged around an outer face of the nonconductive tube. When liquid to be measured is introduced into the nonconductive tube, the electrodes and liquid located between the electrodes define a capacitor to be a concentration sensor. When charge and discharge are repeated relative to the concentration sensor through a switch, a voltage proportional to the ethanol concentration is output based on a discharge current and a resistance.

However, in this case, when the liquid to be measured is constructed by only gasoline, a leak resistance between the electrodes becomes infinite, because gasoline is not conductive. That is, a dielectric constant between the electrodes is approximately equal to zero. In contrast, when liquid such as ethanol or water is mixed in gasoline, the leak resistance is decreased, and the dielectric constant between the electrodes has a positive value.

The leak resistance may affect detection accuracy of the liquid property detecting device. Therefore, the affecting by the leak resistance is required to be eliminated so as to provide higher detection accuracy.

SUMMARY OF THE INVENTION

In view of the foregoing and other problems, it is an object of the present invention to provide a liquid property detecting device.

According to a first example of the present application, a liquid property detecting device includes an electrode, a generator to generate standard voltage applied to the electrode, a switch portion to switch the electrode to charge with the standard voltage or discharge through a grounding, an operation signal output portion, and a signal process portion. The operation signal output portion outputs a first operation signal having a first frequency to the switch portion so as to perform the switching in a first switch period, or a second operation signal having a second frequency to the switch portion so as to perform the switching in a second switch period. The signal process portion processes a detection signal corresponding to a voltage of the electrode when the standard voltage is applied to the electrode. The signal process portion calculates liquid property based on a first detection signal corresponding to the detection signal when the switch portion performs the switching in the first switch period, and a second detection signal corresponding to the detection signal when the switch portion performs the switching in the second switch period. The signal process portion has a gain relative to the detection signal in the calculation of the liquid property. The signal process portion changes the gain in accordance with at least one of the first detection signal and the second detection signal. The gain is configured to be increased as at least one of the first detection signal and the second detection signal is decreased.

Accordingly, detection accuracy can be raised.

According to a second example of the present application, a liquid property detecting device includes an electrode, a generator to generate standard voltage applied to the electrode, a switch portion to switch the electrode to charge with the standard voltage or discharge through a grounding, an operation signal output portion, and a signal process portion. The operation signal output portion outputs a first operation signal having a first frequency to the switch portion so as to perform the switching in a first switch period, or a second operation signal having a second frequency to the switch portion so as to perform the switching in a second switch period. The signal process portion processes a detection signal corresponding to a voltage of the electrode when the standard voltage is applied to the electrode. The signal process portion calculates liquid property based on a first detection signal corresponding to the detection signal when the switch portion performs the switching in the first switch period, and a second detection signal corresponding to the detection signal when the switch portion performs the switching in the second switch period. The signal process portion changes a frequency difference between the first frequency and the second frequency in accordance with at least one of the first detection signal and the second detection signal. The frequency difference is configured to be increased as at least one of the first detection signal and the second detection signal is decreased.

Accordingly, detection accuracy can be raised.

According to a third example of the present application, a liquid property detecting device includes an electrode, a generator to generate standard voltage applied to the electrode, a switch portion to switch the electrode to charge with the standard voltage or discharge through a grounding, an operation signal output portion, and a signal process portion. The operation signal output portion outputs a first operation signal having a first frequency to the switch portion so as to perform the switching in a first switch period, or a second operation signal having a second frequency to the switch portion so as to perform the switching in a second switch period. The signal process portion processes a detection signal corresponding to a voltage of the electrode when the standard voltage is applied to the electrode. The signal process portion calculates liquid property based on a first detection signal corresponding to the detection signal when the switch portion perform the switching in the first switch period, and a second detection signal corresponding to the detection signal when the switch portion performs the switching in the second switch period. The signal process portion changes the standard voltage in accordance with at least one of the first detection signal and the second detection signal. The standard voltage is configured to be increased as at least one of the first detection signal and the second detection signal is decreased.

Accordingly, detection accuracy can be raised.

BRIEF DESCRIPTION OF THE DRAWINGS

The above and other objects, features and advantages of the present invention will become more apparent from the following detailed description made with reference to the accompanying drawings. In the drawings:

FIG. 16 is a flowchart illustrating a determination process of a standard voltage switching in a concentration sensor according to a sixth embodiment;

FIG. 17 is a diagram illustrating a gain relative to a voltage of a switched capacitor circuit of the concentration sensor.

DETAILED DESCRIPTION OF PREFERRED EMBODIMENT (First Embodiment)

An ethanol concentration sensor 1 detects an ethanol concentration in a mixed liquid in which gasoline and ethanol are mixed. The mixed liquid is supplied to an engine 100 of a vehicle as fuel. The ethanol concentration sensor 1 may correspond to a fuel property detecting device.

Figure 1:
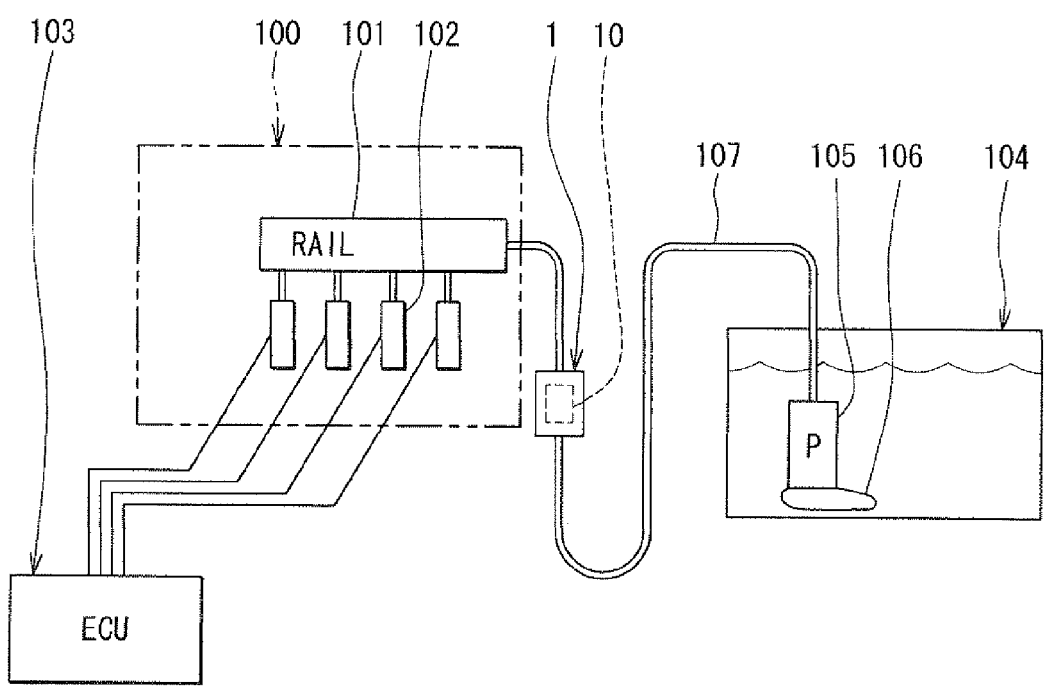
FIG. 1 is a schematic view illustrating a fuel supply system having a concentration sensor according to a first embodiment.

As shown in FIG. 1, fuel is supplied to the engine 100 from a fuel tank 104 through a fuel pipe 107. Fuel in the fuel tank 104 is filtered by a fuel filter 106 and pressurized by a fuel pump 105. The pressurized fuel is stored in a fuel rail 101 of the engine 100, and is distributed to an injector 102 corresponding to a cylinder (not shown). The engine 100 is a four-cylinder engine including four of the injectors 102.

The cylinder 102 is electrically driven by an electronic control unit 103 (ECU). The ECU 103 is constructed by a microcomputer, into which a detection signal is input from the sensor 1. Further, a variety of signals relating to the engine 100 are input into the ECU 103. The ECU 103 outputs a driving signal to the injector 102 based on the input signals. The sensor 1 is located in the fuel pipe 107.

The mixed liquid is used in the engine 100 as fuel. A theoretical air-fuel ratio, heat emitting amount and volatilization characteristics are different between gasoline and ethanol. The fuel tank 104 may be supplied with mixed liquid having a predetermined ratio between gasoline and ethanol, or unmixed liquid including only gasoline. Therefore, ethanol concentration of fuel stored in the fuel tank 104 may be changed when fuel is added to the fuel tank 104.

Ethanol concentration of fuel supplied to the engine 100 is detected by the sensor 1, and a variety of control parameters of the engine 100 are changed based on the detected ethanol concentration, so as to operate the engine 100 in an optimum condition. For example, the optimum condition represents a condition that an amount of toxic content included in exhaust gas is decreased to a minimum level, and that fuel efficiency is improved. The control parameter represents an air-fuel ratio, fuel injection amount, or ignition timing. The ethanol concentration is detected at a location adjacent to the injector 102 for injecting fuel to a combustion chamber (not shown) of the engine 100.

A construction of the sensor 1 will be described.

The sensor 1 includes a housing (not shown) accommodating an electrode portion and a circuit portion. The housing has a fuel passage to be connected to the fuel pipe 107. The electrode portion defines a capacitor by using fuel as a dielectric material.

Figure 2:
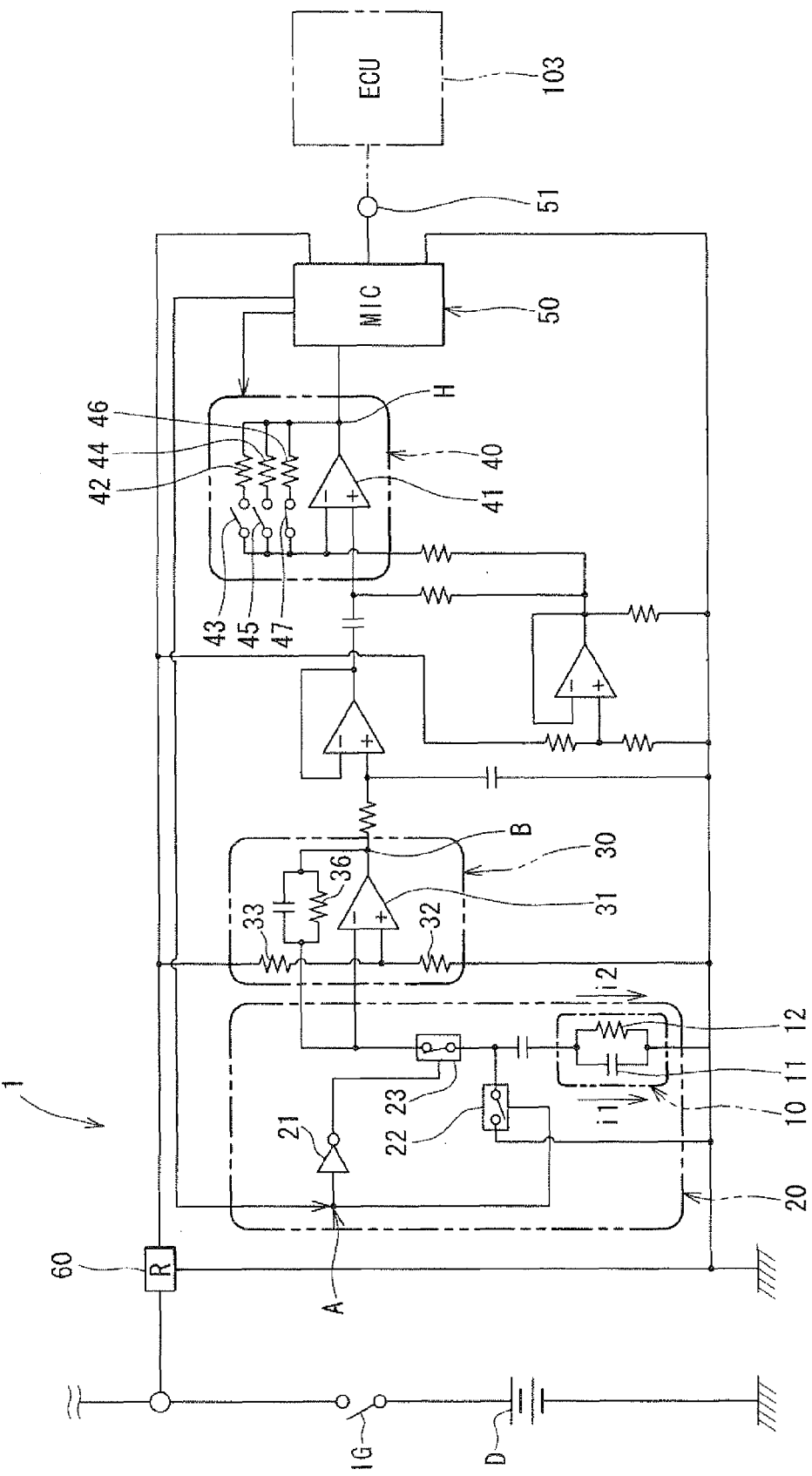
FIG. 2 is a circuit diagram illustrating the concentration sensor.

The circuit portion of the sensor 1 will be described. As shown in FIG. 2, the sensor 1 is activated when power is supplied to the sensor 1 from a vehicle battery D through an ignition switch IG. An output terminal 51 of the sensor 1 is connected to the ECU 103. An ethanol concentration signal detected by the sensor 1 is input into the ECU 103, and the ECU 103 controls the engine 100 by calculating the control parameters such as air-fuel ratio, fuel injection amount, or ignition timing based on the input ethanol concentration signal.

A constant-voltage regulator 60 converts voltage input from the battery D to a supply voltage suitable for activating the sensor 1. The supply voltage stabilized by the regulator 60 is supplied to the circuit portion of the sensor 1. The supply voltage is 5V, for example.

The sensor 1 includes a switched capacitor circuit 20, a standard voltage generator circuit 30, an amplification circuit 40, and a microcomputer 50. The amplification circuit 40 may correspond to a signal process portion.

Figure 3:
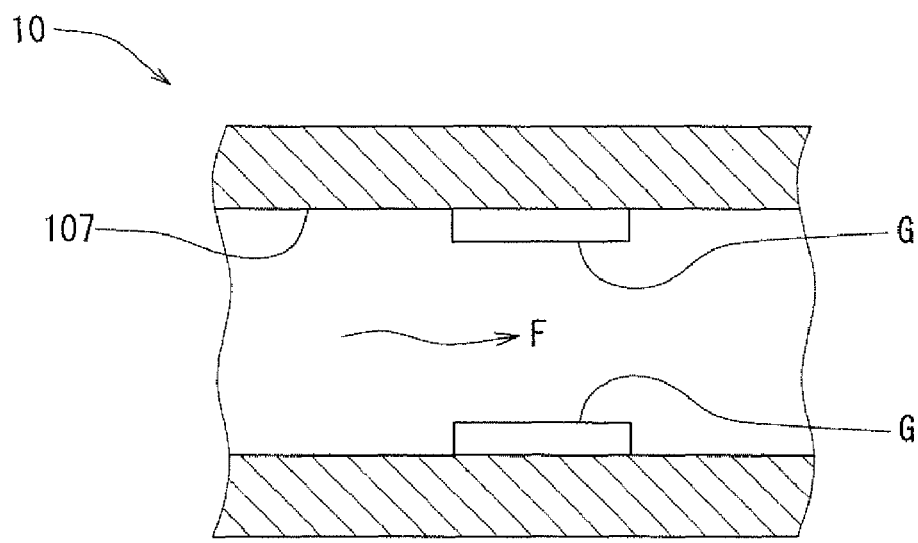
FIG. 3 is a schematic cross-sectional view illustrating a capacitor part of the concentration sensor.

As shown in FIG. 3, the electrode portion of the sensor 1 has a capacitor part 10 having a pair of detection electrodes G. The detection electrodes G oppose to each other through the fuel passage of the fuel pipe 107. When fuel F flows through the fuel passage, space between the detection electrodes G is filled with the fuel F. At this time, the fuel F works as a dielectric material. Thus, a capacitor 11 shown in FIG. 2 is defined by the detection electrodes G and the fuel F.

Further, a leak resistor 12 is defined by the fuel F between the detection electrodes G, and is connected in parallel to the detection electrodes G. As shown in FIG. 2, the capacitor part 10 includes the capacitor 11 and the leak resistor 12 connected in parallel to each other.

Ethanol concentration is measured by measuring a capacitance of the capacitor 11. However, accurate measurement of the ethanol concentration is affected by the leak resistor 12, because a resistance of the leak resistor 12 is varied by fuel properties such as water content. The affecting of the leak resistor 12 is eliminated so as to achieve the accurate measurement of the ethanol concentration.

The switched capacitor circuit 20 includes an inverter 21, a first switch 22, and a second switch 23. The microcomputer 50 applies pulse wave voltage to a point A of the switched capacitor circuit 20, and the pulse wave voltage has two kinds of frequencies. One of the frequencies is a first frequency of a first pulse wave voltage, and the other of the frequencies is a second frequency of a second pulse wave voltage.

The switches 22, 23 are closed when the applied voltage is in high level, and are opened when the applied voltage is in low level. The pulse wave voltage is directly applied to the switch 22 from the microcomputer 50. In contrast, the pulse wave voltage is applied to the switch 23 from the microcomputer 50 through the inverter 21. Therefore, the pulse wave voltages applied to the switch 22 and the switch 23 has the same frequency, but phases of the pulse wave voltages applied to the switch 22 and the switch 23 are opposite from each other.

That is, when the pulse wave voltage applied to the switch 22 is in high level, the pulse wave voltage applied to the switch 23 is in low level. When the pulse wave voltage applied to the switch 22 is in low level, the pulse wave voltage applied to the switch 23 is in high level. Therefore, open/close operation of the switch 22 and open/close operation of the switch 23 are performed at timings opposite from each other. That is, when the switch 22 is opened, the switch 23 is closed. When the switch 22 is closed, the switch 23 is opened.

When the first pulse wave voltage is applied to the point A of the switched capacitor circuit 20 from the microcomputer 50, the switches 22, 23 have the open/close operations at the first frequency. When the second pulse wave voltage is applied to the point A of the switched capacitor circuit 20 from the microcomputer 50, the switches 22, 23 have the open/close operations at the second frequency.

The standard voltage generator circuit 30 includes an operational amplifier 31, a first resistor 32, and a second resistor 33. Due to the standard voltage generator circuit 30, the supply voltage controlled by the constant-voltage regulator 60 is divided to the resistors 32, 33 at a ratio corresponding to resistances of the resistors 32, 33. Thus, the controlled voltage is applied to the switched capacitor circuit 20.

The amplification circuit 40 includes an operational amplifier 41, a first resistor 42, a second resistor 44, and a third resistor 46. The resistors 42, 44, 46 are connected in parallel to each other as a gain resistor. A switch 43, 45, 47 is connected in series with the resistor 42, 44, 46, respectively. When an open/close state of the switch 43, 45, 47 is switched, a resistance of the gain resistor is switched. Thus, a gain of the amplification circuit 40 is switched.

As shown in FIG. 2, the microcomputer 50 outputs a driving signal to the switch 43, 45, 47 of the amplification circuit 40 so as to switch the open/close state. Therefore, the gain of the amplification circuit 40 can be switched by the microcomputer 50.

The microcomputer 50 is activated when the stabilized voltage is supplied from the constant-voltage regulator 60. A signal output from the operational amplifier 41 of the amplification circuit 40 is input into the microcomputer 50. The microcomputer 50 calculates ethanol concentration based on the output signal of the operational amplifier 41, and outputs an electric signal corresponding to the calculation result into the output terminal 51.

The output terminal 51 of the microcomputer 50 is connected to the ECU 103 for controlling the engine 100. The ECU 103 determines the control parameter of the engine 100 and outputs a driving signal to the engine 100 based on the ethanol concentration calculated by the sensor 1 and a variety of physical quantity signals relating to operation states of the engine 100.

A basic operation of the sensor 1 will be described.

When the sensor 1 is activated, the microcomputer 50 alternately applies the first pulse wave voltage and the second pulse wave voltage to the point A of the switched capacitor circuit 20. The first pulse wave voltage has a first frequency f1, and the second pulse wave voltage has a second frequency f2. When the pulse wave voltage is applied to the point A, the switch 22, 23 is opened or closed in a period sync with the frequency f1, f2, and open/close state of the switches 22, 23 are opposite from each other.

As shown in FIG. 2, when the switch 22 is opened, and when the switch 23 is closed, a standard voltage E is applied to the capacitor part 10 from the standard voltage generator circuit 30 through the switch 23. Further, current i1 passes through the capacitor 11, and current i2 passes through the leak resistor 12.

The current i1 starts to pass through the capacitor 11 immediately after the voltage E is applied, and the current i1 is reduced to zero when charge of the capacitor 11 is finished. In contrast, the current i2 passing through the leak resistor 12 in parallel to the capacitor 11 has a constant value while the standard voltage E is applied to the capacitor part 10.

When the switch 22 is closed, and when the switch 23 is opened, the standard voltage E is not applied to the capacitor part 10 from the standard voltage generator circuit 30 through the switch 23. The current i1 flows from the capacitor 11 to a ground. A flowing direction of the current i1 is opposite, compared with a case when the switch 22 is opened and when the switch 23 is closed. When discharge of the capacitor 11 is finished, the current becomes zero. The current i2 passing through the leak resistor 12 is zero, when the switch 22 is closed, and when the switch 23 is opened.

An output voltage Vb of a point B of the operational amplifier 31 will be described, when the switches 22, 23 are switched to have the frequency f1, f2.

Formula 1 represents an average value of the current i2, in which the leak resistor 12 has a resistance Rp.

$$i2 = 0.5 \times E/Rp \qquad \text{Formula 1}$$

Formula 2 represents a charge amount $\Delta Q$ stored in the capacitor 11, in which the capacitor 11 has a capacitance Cp.

$$\Delta Q = Cp \times E \qquad \text{Formula 2}$$

Formula 3 represents an average value of the current i1 by differentiating Formula 2, in which a period T is a reciprocal of a frequency f (T=1/f).

$$i1 = \Delta Q/T = Cp \times E/T = Cp \times E \times f \quad \text{Formula 3}$$

As shown in Formula 3, the current i1 discharged from the capacitor 11 is proportional to the frequency f of the pulse wave voltage applied to the point A of the switched capacitor circuit 20.

Formula 4 represents the voltage Vb of the point B by using Formula 1 and Formula 3, in which a resistor 36 has a resistance Rg.

$$\begin{aligned} Vb &= E + Rg \times (i1 + i2) \quad \text{Formula 4}\\ &= E + Rg \times (Cp \times E/T + 0.5 \times E/Rp)\\ &= E \times (1 + 0.5 \times Rg/Rp + Rg \times Cp \times f) \end{aligned}$$

The resistance Rp of the leak resistor 12 of the capacitor part 10 is included in Formula 4 representing the voltage Vb of the point B. The capacitor part 10 is a detector of the sensor 1, and the voltage Vb represents a level of an output signal output from the capacitor part 10. The resistance Rp of the leak resistor 12 is varied by a ratio of conductive impurity relative to gasoline, and the voltage Vb is changed by the varied resistance Rp.

The microcomputer 50 alternately applies the first pulse wave voltage having the first frequency f1 and the second pulse wave voltage having the second frequency f2 to the switched capacitor circuit 20. Therefore, two of the voltages $Vb_{f1}$, $Vb_{f2}$ are obtained. The voltage $Vb_{f1}$ corresponds to the voltage Vb when the applied pulse wave voltage has the first frequency f1, and the voltage $Vb_{f2}$ corresponds to the voltage Vb when the applied pulse wave voltage has the second frequency f2. The period T of the charge/discharge of the capacitor part 10 is not fixed to a single value, because the frequency f of the open/close operation of the switch 22, 23 is switched to the first frequency f1 or the second frequency f2.

Formula 5 represents the voltage $Vb_{f1}$ of the point B, when the switch 22, 23 is opened or closed with the first frequency f1, while the sensor 1 is activated.

$$Vb_{f1} = E \times (1 + 0.5 \times Rg/Rp + Rg \times Cp \times f1) \quad \text{Formula 5}$$

Formula 6 represents the voltage $Vb_{f2}$ of the point B, when the switch 22, 23 is opened or closed with the second frequency f2.

$$Vb_{f2} = E \times (1 + 0.5 \times Rg/Rp + Rg \times Cp \times f2) \quad \text{Formula 6}$$

Formula 7 represents a difference between the voltage $Vb_{f1}$ and the voltage $Vb_{f2}$.

$$Vb_{f1} - Vb_{f2} = E \times (f1 - f2) \times Rg \times Cp \quad \text{Formula 7}$$

The resistance Rp of the leak resistor 12 is eliminated in Formula 7 representing the voltage Vb of the point B. The voltage Vb corresponds to an output signal of the ethanol concentration. Therefore, factor affecting the detection accuracy of the sensor 1 can be eliminated.

The voltage Vb is an electric signal representing the ethanol concentration. Due to the amplification circuit 40, the voltage Vb is amplified so as to be processed by the microcomputer 50, and the amplified voltage is input into the microcomputer 50 as a voltage $V_{50}$ of a point H shown in FIG. 2.

Figure 4:
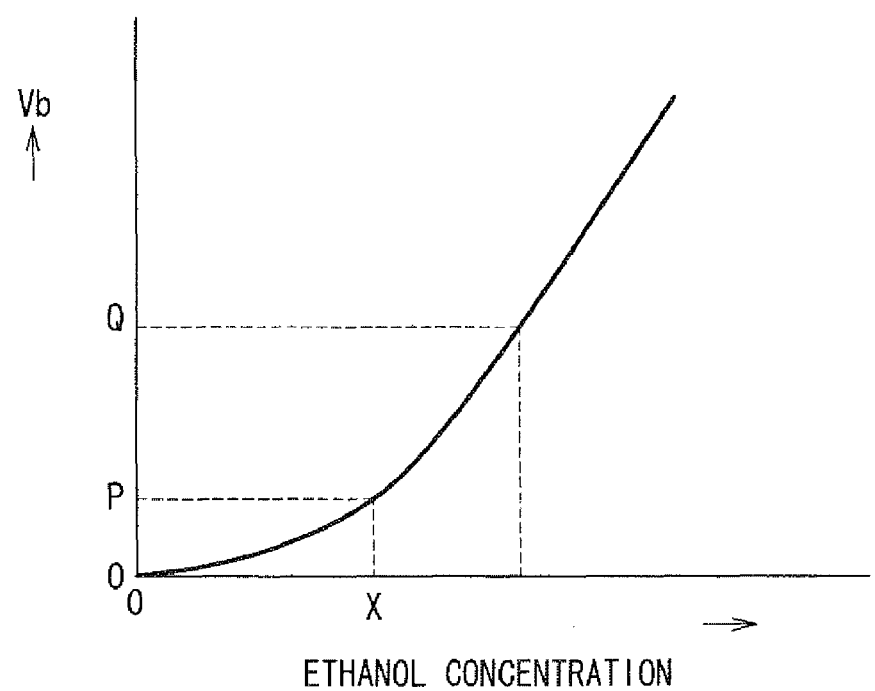
FIG. 4 is a graph illustrating a relationship between an ethanol concentration and a voltage of a switched capacitor circuit of the concentration sensor.

The voltage Vb of the point B is directly proportional to the ethanol concentration. As shown in FIG. 4, when the ethanol concentration is equal to or higher than a predetermined value X, a relationship between the voltage Vb and the ethanol concentration is approximately linear. In contrast, when the ethanol concentration is lower than the predetermined value X, the relationship between the voltage Vb and the ethanol concentration is exponential. A variation amount of the voltage Vb relative to a variation amount of the ethanol concentration is small in the exponential relationship, compared with the liner relationship. That is, when the ethanol concentration is low, resolution is small.

When the ethanol concentration is lower than the predetermined value X, the ethanol concentration is difficult to be accurately calculated based on the voltage Vb of the point B, even if the factor affecting the detection accuracy of the sensor 1 is eliminated.

In a comparison example, a gain to be an amplifying rate of an amplification circuit is set in a manner that a voltage representing the ethanol concentration does not go beyond an allowable voltage range of a microcomputer when the ethanol concentration is at the maximum level. In a case that the ethanol concentration is low, if the gain is increased so as to raise the voltage, the voltage may go beyond the allowable voltage range when the ethanol concentration becomes high. Thus, accurate calculation of the ethanol concentration is impossible by the comparison example.

According to the sensor 1 of the first embodiment, the gain of the amplification circuit 40 is changeable. The gain is changed in accordance with the voltage Vb of the point B. Specifically, as shown in FIG. 4, when the voltage Vb is lower than a first value P representing a border between the linear relationship and the exponential relation, the amplification circuit 40 has a gain L. When the voltage Vb is equal to or higher than the first value P, and when the voltage Vb is lower than a second value Q, the amplification circuit 40 has a gain M. When the voltage Vb is equal to or higher than the second value Q, the amplification circuit 40 has a gain N. The gain L is larger than gain M, and the gain M is larger than gain N (L>M>N).

When the voltage Vb corresponding to a detection signal of the ethanol concentration is low, the gain of the amplification circuit 40 is switched to become large. The gain is set by the microcomputer 50 based on at least one of the voltage $Vb_{f1}$ and voltage $Vb_{f2}$. The microcomputer 50 outputs a driving signal to the amplification circuit 40 to switch open/close state of the switch 43, 45, 47 so as to set the gain.

Specifically, as shown in FIG. 2, when the gain L is set by selecting the resistor 46, the switch 47 is closed, and the switches 45, 43 are opened. When the gain M is set by selecting the resistor 44, the switch 45 is closed, and the switches 47, 43 are opened. When the gain N is set by selecting the resistor 42, the switch 43 is closed, and the switches 47, 45 are opened.

Figure 5:
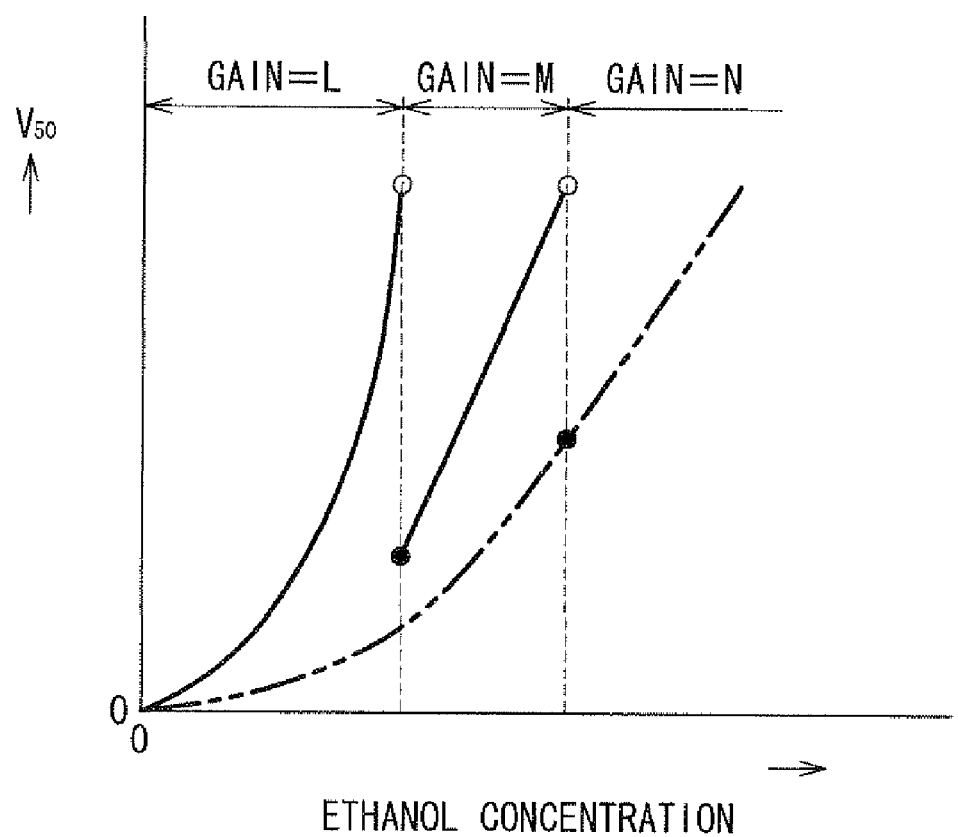
FIG. 5 is a graph illustrating a relationship between an ethanol concentration and a voltage of a microcomputer of the concentration sensor.

FIG. 5 shows a relationship between the ethanol concentration and the voltage $V_{50}$ of the microcomputer 50, when the gain is switched based on the voltage $Vb_{f1}$, $Vb_{f2}$. A double-chain line of FIG. 5 represents the voltage $V_{50}$ when the amplification circuit 40 is fixed to have the gain N. A solid line of FIG. 5 represents the voltage $V_{50}$ when the gain of the amplification circuit 40 is switched based on the voltage Vb.

When the voltage Vb is higher than zero, and when the voltage Vb is lower than the first value P, the gain L is selected and the voltage $V_{50}$ is shown in the solid line. When the voltage Vb is equal to or higher than the first value P, and when the voltage Vb is lower than the second value Q, the gain M is selected and the voltage $V_{50}$ is shown in the solid line. When the voltage Vb is equal to or higher than the second value Q, the gain N is selected and the voltage $V_{50}$ is shown in the double-chain line.

According to the first embodiment, when a variation of the voltage $V_{50}$ corresponding to a variation of the ethanol concentration is small (0<Vb<P), the voltage $V_{50}$ is increased by increasing the gain, so as to raise the solution. Thus, accurate calculation of the ethanol concentration can be possible.

The gain of the amplification circuit 40 is switched among three levels. Alternatively, the gain of the amplification circuit 40 may be switched between two levels, or among four or more levels.

(Second Embodiment)

Figure 6:
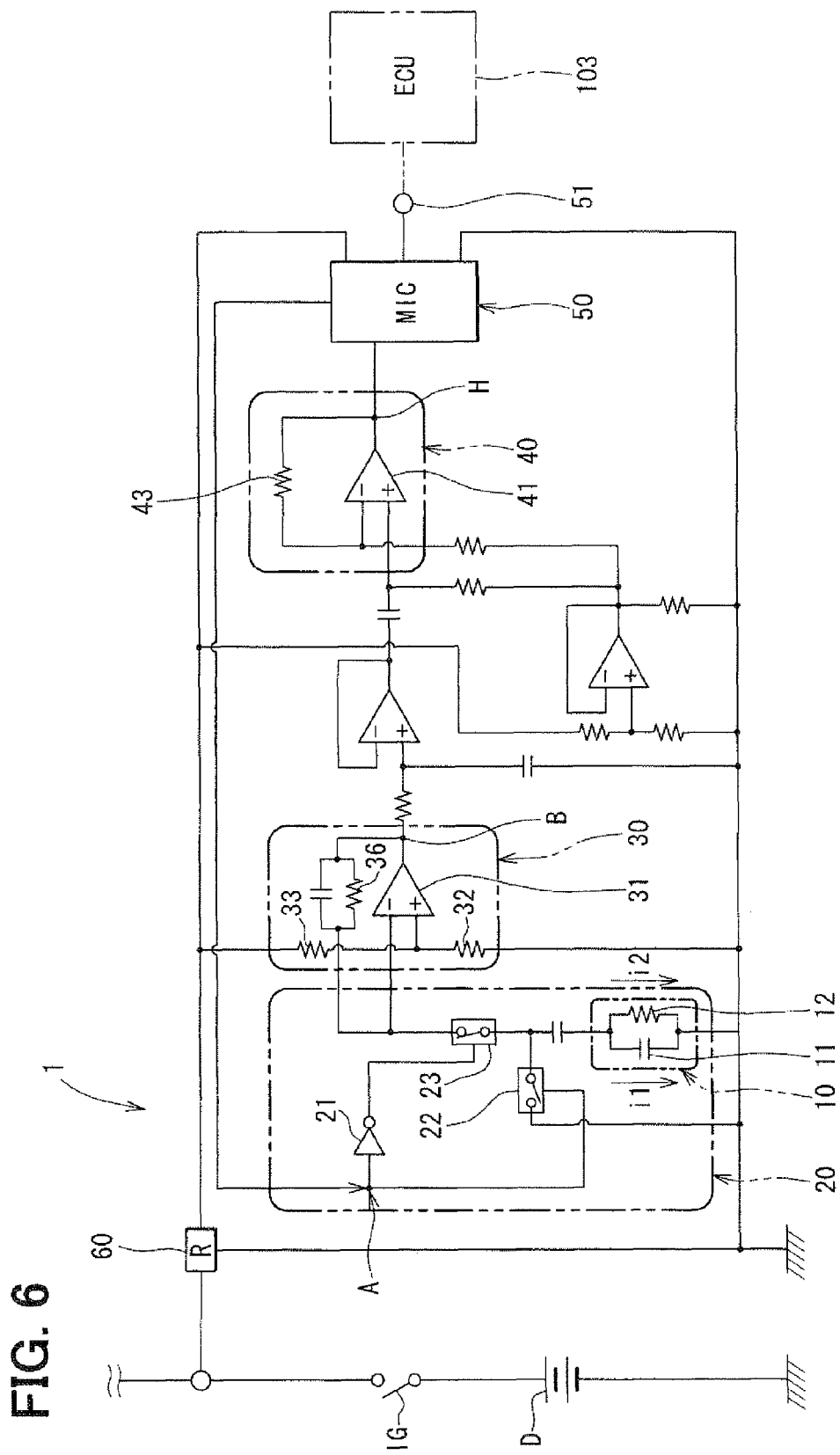
FIG. 6 is a circuit diagram illustrating a concentration sensor according to a second embodiment.

As shown in FIG. 6, an amplification circuit 40 of an ethanol concentration sensor 1 has a single resistor 43 so as to fix a gain of the amplification circuit 40, in a second embodiment.

In contrast, plural kinds of frequency difference Δf between a first frequency f1 and a second frequency f2 are prepared, in the second embodiment. The frequency difference Δf represents a difference of the frequencies f1, f2 of pulse wave voltages applied to a point A of a switched capacitor circuit 20 from a microcomputer 50. The frequency difference Δf is changed in accordance with situations.

Characteristics of the sensor 1 of the second embodiment will be described.

As shown in Formula 7: $Vb_{f1}-Vb_{f2}=E\times(f1-f2)\times Rg\times Cp$, a difference of the voltages $Vb_{f1}$, $Vb_{f2}$ of the point B of the switched capacitor circuit 20 is proportional to the frequency difference Δf (Δf=f1−f2). The difference of the voltages $Vb_{f1}$, $Vb_{f2}$ corresponds to a detection signal of ethanol concentration. Therefore, if the frequency difference Δf is increased, level of the detection signal of ethanol concentration is increased.

The frequency difference Δf is increased in the second embodiment, while a gain of the amplification circuit 40 is increased in the first embodiment. Therefore, the ethanol concentration can be accurately detected, when the ethanol concentration is low, and when the ethanol concentration and the voltage Vb have an exponential relationship of FIG. 4.

Figures 7, 8:
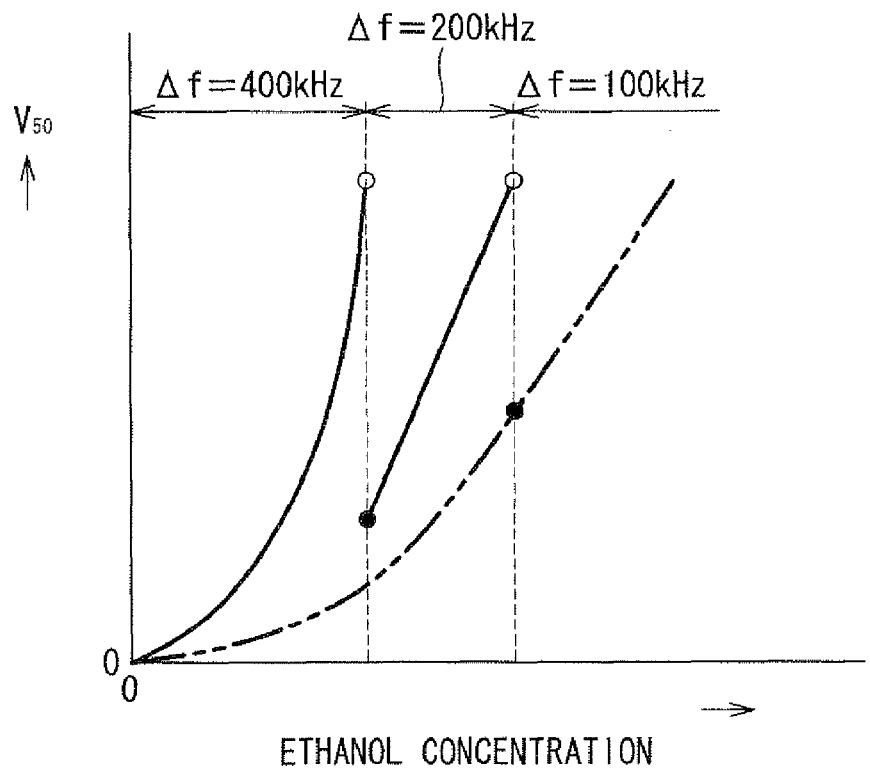
FIG. 7 is a diagram illustrating a frequency combination relative to the voltage of the switched capacitor circuit.
FIG. 8 is a graph illustrating a relationship between an ethanol concentration and a voltage of a microcomputer of the concentration sensor.

Specifically, as shown in FIG. 7, when the voltage Vb is lower than a first value P representing a border between the linear relationship and the exponential relation, the first frequency f1 is set to be 500 kHz, and the second frequency f2 is set to be 100 kHz, thereby the frequency difference Δf is set to be 400 kHz. When the voltage Vb is equal to or higher than the first value P, and when the voltage Vb is lower than a second value Q, the first frequency f1 is set to be 500 kHz, and the second frequency f2 is set to be 300 kHz, thereby the frequency difference Δf is set to be 200 kHz. When the voltage Vb is equal to or higher than the second value Q, the first frequency f1 is set to be 500 kHz, and the second frequency f2 is set to be 400 kHz, thereby the frequency difference Δf is set to be 100 kHz.

The microcomputer 50 obtains at least one of the voltages $Vb_{f1}$, $Vb_{f2}$, and sets the first frequency f1 and the second frequency f2 based on the voltage $Vb_{f1}$, $Vb_{f2}$. The pulse wave voltages having the set frequencies f1, f2 are applied to the point A. Therefore, the frequency difference Δf can be switched.

The ethanol concentration and a voltage $V_{50}$ of the microcomputer 50 have a relationship shown in FIG. 8. A double-chain line of FIG. 8 represents a case in which the frequency difference Δf is fixed to 100 kHz.

According to the second embodiment, when a variation of the voltage $V_{50}$ corresponding to a variation of the ethanol concentration is small (0<Vb<P), the variation of the voltage $V_{50}$ is increased by increasing the frequency difference Δf, so as to raise the solution. Thus, accurate calculation of the ethanol concentration can be possible.

(Third Embodiment)

Figure 9:
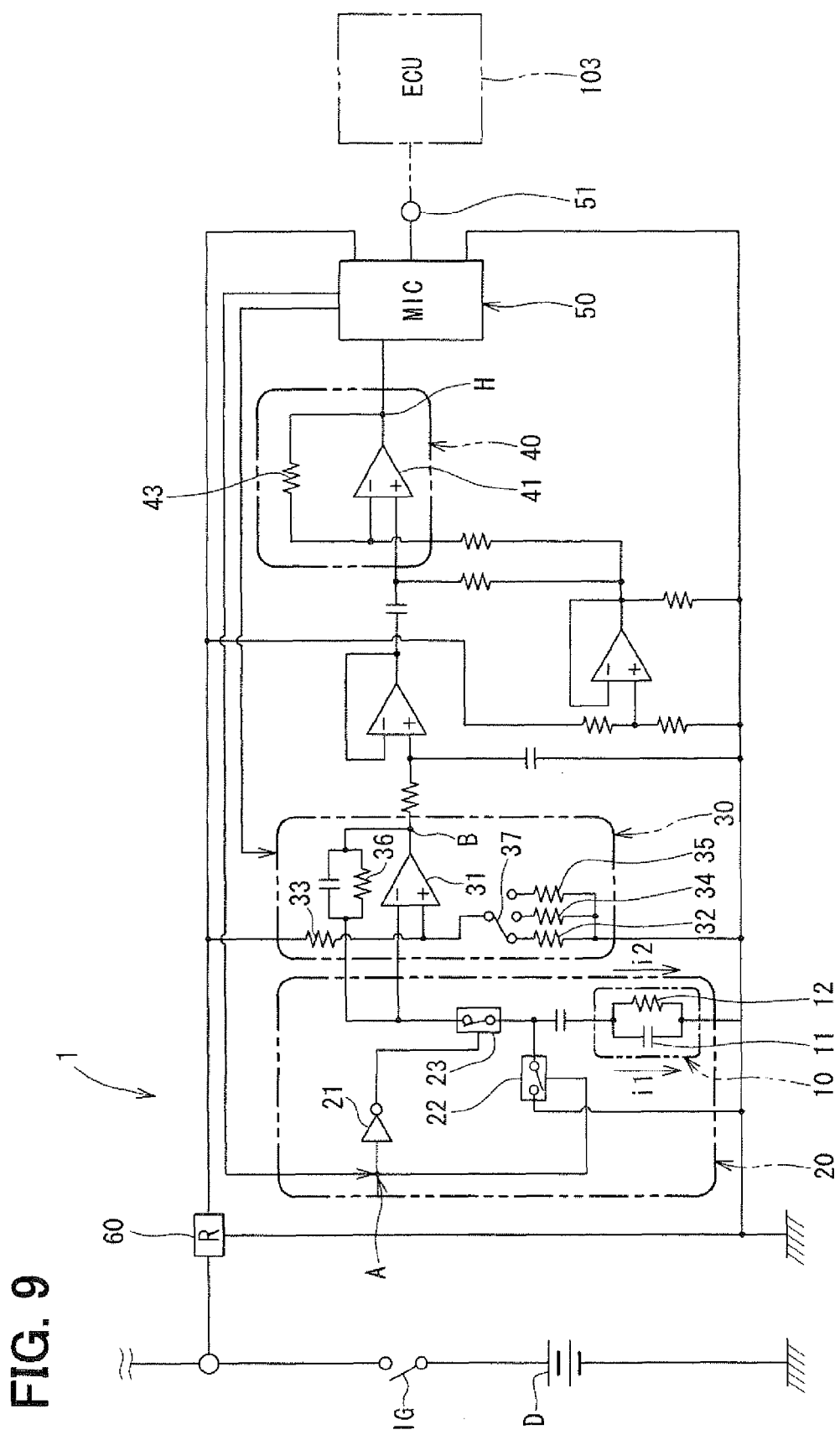
FIG. 9 is a circuit diagram illustrating a concentration sensor according to a third embodiment.

As shown in FIG. 9, an amplification circuit 40 of an ethanol concentration sensor 1 has a single resistor 43 so as to fix a gain of the amplification circuit 40, in a third embodiment.

In contrast, plural kinds of standard voltage E applied to the switched capacitor circuit 20 are prepared, in the third embodiment. The standard voltage E is controlled and output by a standard voltage generator circuit 30. The standard voltage E is changed in accordance with situations.

Characteristics of the sensor 1 of the third embodiment will be described.

As shown in Formula 7: $Vb_{f1}-Vb_{f2}=E\times(f1-f2)\times Rg\times Cp$, a difference of the voltages $Vb_{f1}$, $Vb_{f2}$ of the point B of the switched capacitor circuit 20 is proportional to the standard voltage E. The difference of the voltages $Vb_{f1}$, $Vb_{f2}$ corresponds to a detection signal of ethanol concentration. Therefore, if the standard voltage E is increased, level of the detection signal of ethanol concentration is increased.

The standard voltage E is increased in the third embodiment, while a gain of the amplification circuit 40 is increased in the first embodiment. Therefore, the ethanol concentration can be accurately detected, when the ethanol concentration is low, and when the ethanol concentration and the voltage Vb have an exponential relationship of FIG. 4.

Figures 10, 11:
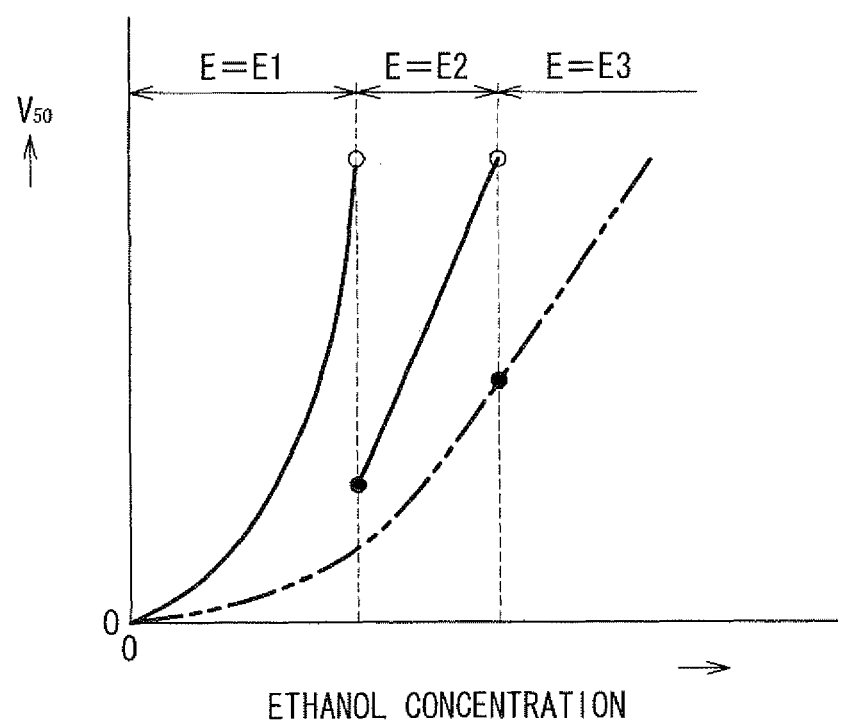
FIG. 10 is a diagram illustrating a standard voltage relative to the voltage of the switched capacitor circuit.
FIG. 11 is a graph illustrating a relationship between an ethanol concentration and a voltage of a microcomputer of the concentration sensor.

Specifically, as shown in FIG. 10, when the voltage Vb is lower than a first value P representing a border between the linear relationship and the exponential relation (0<Vb<P), the standard voltage E is set to be a value E1. When the voltage Vb is equal to or higher than the first value P, and when the voltage Vb is lower than a second value Q (P≦Vb<Q), the standard voltage E is set to be a value E2. When the voltage Vb is equal to or higher than the second value Q (Q≦Vb), the standard voltage E is set to be a value E3. The values E1, E2 and E3 have a relationship of E1>E2>E3.

The microcomputer 50 obtains at least one of the voltages $Vb_{f1}$, $Vb_{f2}$, and sets the standard voltage E based on the voltage $Vb_{f1}$, $Vb_{f2}$. The microcomputer 50 outputs a driving signal to a switch 37 of the standard voltage generator circuit 30 shown in FIG. 9. The switch 37 is connected to one of resistors 32, 34, 35 corresponding to the set value E1, E2, E3. Thus, the standard voltage E can be switched.

The standard voltage E is changed based on at least one of the voltages $Vb_{f1}$, $Vb_{f2}$. The ethanol concentration and a voltage $V_{50}$ of the microcomputer 50 have a relationship shown in FIG. 11. A double-chain line of FIG. 11 represents a case in which the standard voltage E is fixed to the value E3.

According to the third embodiment, when a variation of the voltage $V_{50}$ corresponding to a variation of the ethanol concentration is small (0<Vb<P), the variation of the voltage $V_{50}$ is increased by increasing the standard voltage E, so as to raise the solution. Thus, accurate calculation of the ethanol concentration can be possible.

(Fourth Embodiment)

An ethanol concentration sensor 1 has a determining portion to determine a switching of gain to be normally performed or not, in a fourth embodiment.

A microcomputer 50 of the sensor 1 switches a gain of an amplification circuit 40 in accordance with a voltage Vb corresponding to a detection signal of ethanol concentration, so as to improve detection accuracy. The sensor 1 further includes the determining portion to determine the gain to be normally switched or not.

Figures 12, 13:
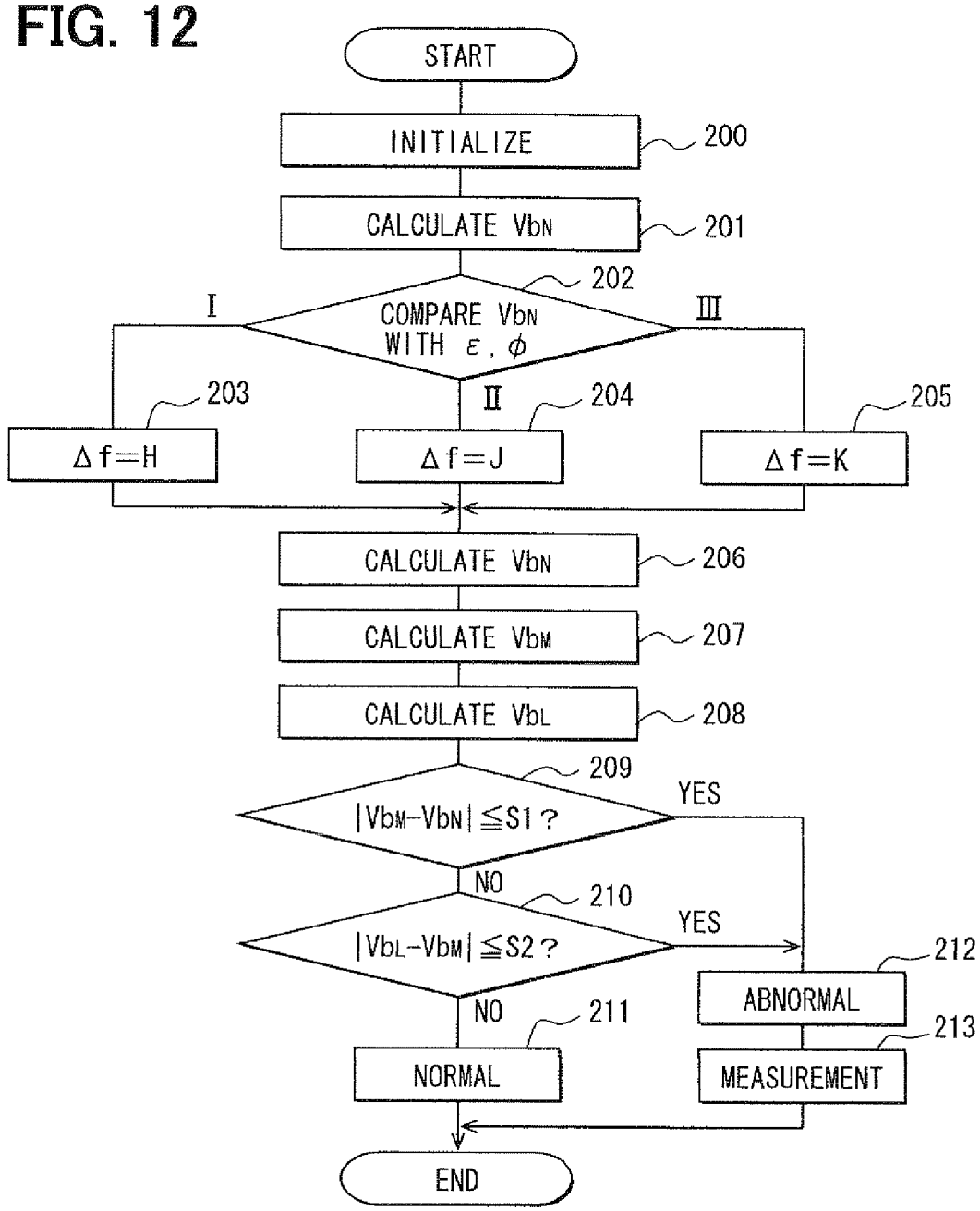
FIG. 12 is a flowchart illustrating a determination process of a gain switching in a concentration sensor according to a fourth embodiment.
FIG. 13 is a diagram illustrating a frequency difference relative to a voltage of a switched capacitor circuit of the concentration sensor.

A determination process will be described with reference to FIG. 12. The determination process is performed based on a program stored in the microcomputer 50.

The determination process is performed at the same frequency as a detection process of ethanol concentration. For example, the determination process and the detection process are alternately performed. The detection process is similar to that of the first embodiment.

When an ignition switch IG is turned on, the determination process is started to determine the gain switching to be normal or not. At this time, the microcomputer 50 performs an initialization at step 200.

The microcomputer 50 calculates a voltage $Vb_N$ by using a gain N and the voltage Vb corresponding to the ethanol concentration at step 201. The gain N is the smallest gain among the gains L, M, N.

The voltage $Vb_N$ is compared with thresholds $\in$, $\phi$ at step 202. As shown in FIG. 13, when the voltage $Vb_N$ is larger than zero, and when the voltage $Vb_N$ is equal to or smaller than the threshold $\in$ ($0 < Vb_N \leq \in$), the voltage $Vb_N$ is determined to be in an area I. When the voltage $Vb_N$ is larger than the threshold $\in$, and when the voltage $Vb_N$ is equal to or smaller than the threshold $\phi$ ($0 < Vb_N \leq \phi$), the voltage $Vb_N$ is determined to be in an area II. When the voltage $Vb_N$ is larger than the threshold $\phi$ ($\phi < Vb_N$), the voltage $Vb_N$ is determined to be in an area III.

Because the smallest gain N is used in the calculation at step 201, the calculated voltage $Vb_N$ is always in a dynamic range corresponding to a detection range. Therefore, the voltage $Vb_N$ is determined to be in one of the areas I, II, III.

When the voltage $Vb_N$ is determined to be in the area I, a frequency difference $\Delta f$ between frequencies f1, f2 of switches 22, 23 of a switched capacitor circuit 20 is set to have a value H larger than an ordinary value J at step 203.

When the voltage $Vb_N$ is determined to be in the area II, the frequency difference $\Delta f$ between the frequencies f1, f2 of the switches 22, 23 of the switched capacitor circuit 20 is set to have the ordinary value J at step 204.

When the voltage $Vb_N$ is determined to be in the area III, the frequency difference $\Delta f$ between the frequencies f1, f2 of the switches 22, 23 of the switched capacitor circuit 20 is set to have a value K smaller than the ordinary value J at step 205.

The voltage $Vb_N$ is recalculated by using the gain N and the selected value H, J, K as the frequency difference $\Delta f$ at step 206. The voltage $Vb_N$ is an electric signal representing the ethanol concentration.

A voltage $Vb_M$ is calculated by using the gain M and the selected value H, J, K as the frequency difference $\Delta f$ at step 207. The voltage $Vb_M$ is an electric signal representing the ethanol concentration.

A voltage $Vb_L$ is calculated by using the gain L and the selected value H, J, K as the frequency difference $\Delta f$ at step 208. The voltage $Vb_L$ is an electric signal representing the ethanol concentration.

Because the smallest gain N is used at step 201, the calculated voltage Vb is always in the dynamic range corresponding to the detection range. Therefore, the determination of the voltage $Vb_N$ can be accurately performed at step 202.

Further, because the frequency difference $\Delta f$ is selected at one of steps 203, 204, 205 based on the determination result at step 202, the voltage $Vb_N$, $Vb_M$, $Vb_L$ calculated at step 206, 207, 208 can be made larger in the dynamic range. Therefore, accurate determination can be performed.

An absolute value of a difference between the calculated voltages $Vb_N$, $Vb_M$ is compared with a threshold S1 at step 209.

An absolute value of a difference between the calculated voltages $Vb_M$, $Vb_L$ is compared with a threshold S2 at step 210.

When the absolute value of the difference between the calculated voltages $Vb_N$, $Vb_M$ is larger than the threshold S1, the absolute value of the difference between the calculated voltages $Vb_M$, $Vb_L$ is compared with the threshold S2 at step 210. When the absolute value of the difference between the calculated voltages $Vb_M$, $Vb_L$ is larger than the threshold S2, the gain switching is determined to be normal at step 211.

In contrast, when the absolute value of the difference between the calculated voltages $Vb_N$, $Vb_M$ is equal to or smaller than the threshold S1, or when the absolute value of the difference between the calculated voltages $Vb_M$, $Vb_L$ is equal to or smaller than the threshold S2, the gain switching is determined to be abnormal at step 212. Therefore, a necessary measurement is conducted at step 213.

The output voltages $Vb_L$, $Vb_M$, $Vb_N$ corresponding to the ethanol concentration are calculated by using the gains L, M, N (L>M>N) at step 206, 207, 208, respectively. The frequency difference $\Delta f$ is selected at step 203, 204, 205 in a manner that the voltage Vb is not saturated if the voltage Vb is calculated by using the largest gain L. Thus, the voltage Vb is included in the dynamic range corresponding to the detection range. Therefore, the voltage $Vb_L$, $Vb_M$, $Vb_N$ has a substantial true value.

When the gain switching is normally performed by the amplification circuit 40, the voltages $Vb_L$, $Vb_M$, $Vb_N$ are determined by the gains L, M, N. That is, a ratio of the voltages $Vb_L$:$Vb_M$:$Vb_N$ is approximately equal to a ratio of the gains L:M:N. In contrast, when the gain switching of the amplification circuit 40 has abnormality, the ratio of the voltages $Vb_L$:$Vb_M$:$Vb_N$ is different from the ratio of the gains L:M:N.

The voltage $Vb_L$, $Vb_M$, $Vb_N$ corresponds to a calibration voltage. For example, in a case that the ratio of the gains is approximately equal to 1:2:8, when the ratio of the voltages is approximately equal to 1:2:5, a setting of the gain may be determined to be abnormal. Further, when the ratio of the voltages is approximately equal to 1:1:8, a switching of the gain may be determined to be abnormal.

Therefore, when the absolute value of the difference between the calculated voltages $Vb_N$, $Vb_M$ is approximately equal to the threshold S1 set based on the gains N, M, and when the absolute value of the difference between the calculated voltages $Vb_M$, $Vb_L$ is approximately equal to the threshold S2 set based on the gains M, L, the gain switching can be determined to be normal.

According to the fourth embodiment, when a variation of the voltage Vb corresponding to a variation of the ethanol concentration is small (0<Vb<P), a variation of the voltage $V_{50}$ is increased by increasing the gain, so as to raise the solution. Thus, accurate calculation of the ethanol concentration can be possible. Further, the gain switching can be determined to be normal or not.

(Fifth Embodiment)

An ethanol concentration sensor 1 has a determining portion to determine a switching of frequency difference to be normally performed or not, in a fifth embodiment.

A microcomputer 50 of the sensor 1 switches a frequency difference $\Delta f$ defined between two frequencies of pulse wave voltages applied to a point A of a switched capacitor circuit 20 in accordance with a voltage Vb corresponding to a detection signal of ethanol concentration, so as to improve detection accuracy. In the second embodiment, the frequency difference $\Delta f$ is selected among 400 kHz, 200 kHz and 100 kHz. In the fifth embodiment, the ethanol sensor 1 further includes the determining portion to determine the frequency difference $\Delta f$ to be normally switched or not.

Figures 14, 15:
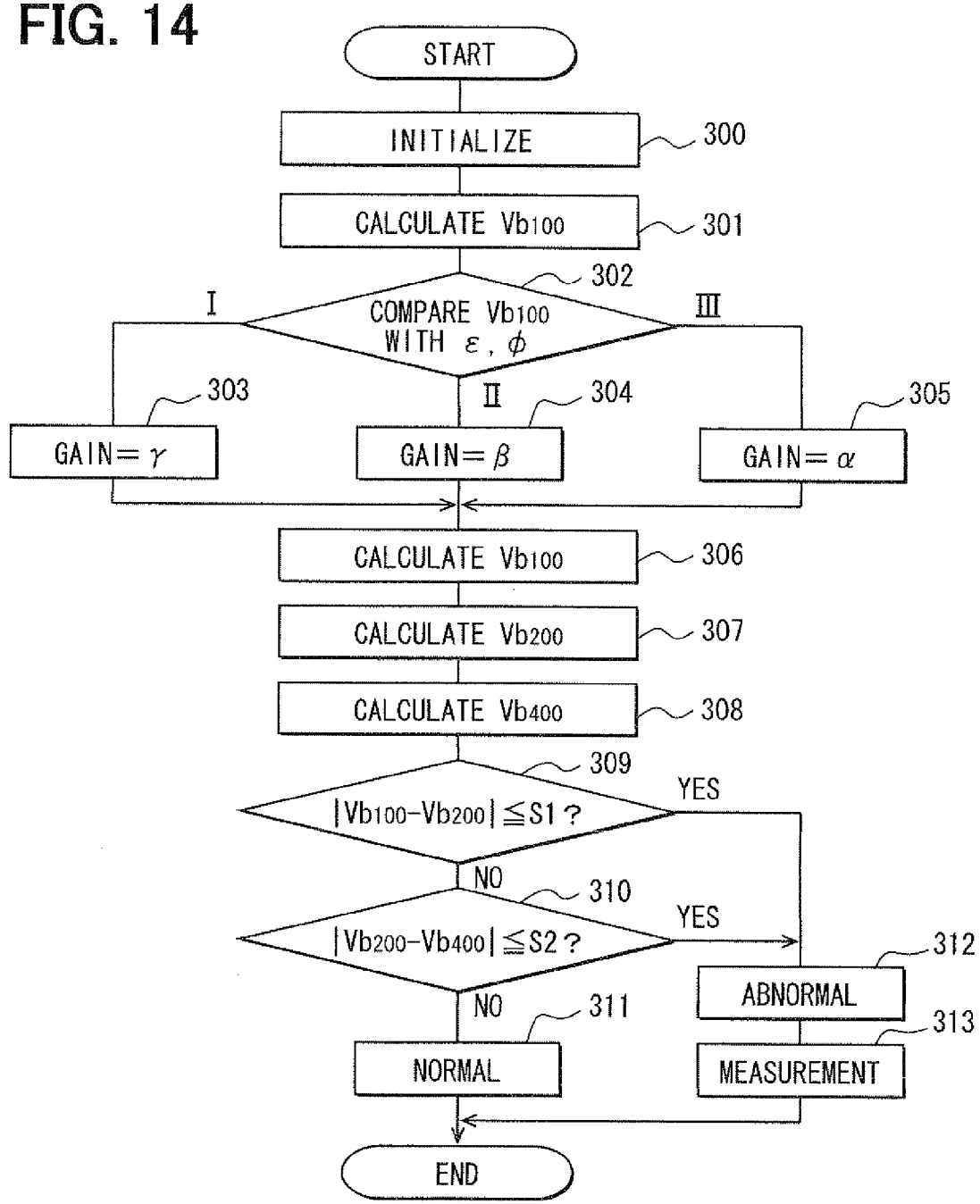
FIG. 14 is a flowchart illustrating a determination process of a frequency difference switching in a concentration sensor according to a fifth embodiment.
FIG. 15 is a diagram illustrating a gain relative to a voltage of a switched capacitor circuit of the concentration sensor.

A determination process will be described with reference to FIG. 14. The determination process is performed based on a program stored in the microcomputer 50.

The determination process is performed at the same frequency as a detection process of ethanol concentration. For example, the determination process and the detection process are alternately performed. The detection process is similar to that of the second embodiment.

When an ignition switch IG is turned on, the determination process is started to determine the switching of the frequency difference $\Delta f$ to be normal or not. At this time, the microcomputer 50 performs an initialization at step 300.

The microcomputer 50 calculates a voltage $Vb_{100}$ by using a frequency difference $\Delta f=100$ kHz and the voltage Vb corresponding to the ethanol concentration at step 301. The frequency difference $\Delta f$ is set to be the smallest ($\Delta f=100$ kHz) among the three selectable frequency differences.

The voltage $Vb_{100}$ is compared with thresholds $\in$, $\phi$ at step 302. As shown in FIG. 15, when the voltage $Vb_{100}$ is larger than zero, and when the voltage $Vb_{100}$ is equal to or smaller than the threshold $\in (0<Vb_{100}\leq\in)$, the voltage $Vb_{100}$ is determined to be in an area I. When the voltage $Vb_{100}$ is larger than the threshold $\in$, and when the voltage $Vb_{100}$ is equal to or smaller than the threshold $\phi (0<Vb_{100}\leq\phi)$, the voltage $Vb_{100}$ is determined to be in an area II. When the voltage $Vb_{100}$ is larger than the threshold $\phi (\phi<Vb_{100})$, the voltage $Vb_{100}$ is determined to be in an area III.

When the voltage $Vb_{100}$ is determined to be in the area I, a gain used for calculating the output voltage Vb is set to have a value $\gamma$ larger than an ordinary value $\beta$ at step 303.

When the voltage $Vb_{100}$ is determined to be in the area II, the gain used for calculating the output voltage Vb is set to have the ordinary value $\beta$ at step 304.

When the voltage $Vb_{100}$ is determined to be in the area III, the gain used for calculating the output voltage Vb is set to have a value $\alpha$ smaller than the ordinary value $\beta$ at step 305.

The voltage $Vb_{100}$ is recalculated by using the frequency difference $\Delta f=100$ kHz and the selected gain $\gamma$, $\beta$, $\alpha$ at step 306.

A voltage $Vb_{200}$ is calculated by using the frequency difference $\Delta f=200$ kHz and the selected gain $\gamma$, $\beta$, $\alpha$ at step 307.

A voltage $Vb_{400}$ is calculated by using the frequency difference $\Delta f=400$ kHz and the selected gain $\gamma$, $\beta$, $\alpha$ at step 308.

Because the smallest frequency difference $\Delta f=100$ kHz is used at step 301, the calculated voltage Vb is always in a dynamic range corresponding to a detection range. Therefore, the determination of the voltage $Vb_{100}$ can be accurately performed at step 302.

Further, because the gain is selected at one of steps 303, 304, 305 based on the determination result at step 302, the voltage $Vb_{100}$, $Vb_{200}$, $Vb_{400}$ calculated at step 306, 307, 308 can be made larger in the dynamic range. Therefore, accurate determination can be performed.

An absolute value of a difference between the calculated voltages $Vb_{100}$, $Vb_{200}$ is compared with a threshold S1 at step 309.

An absolute value of a difference between the calculated voltages $Vb_{200}$, $Vb_{400}$ is compared with a threshold S2 at step 310.

When the absolute value of the difference between the calculated voltages $Vb_{100}$, $Vb_{200}$ is larger than the threshold S1, the absolute value of the difference between the calculated voltages $Vb_{200}$, $Vb_{400}$ is compared with the threshold S2 at step 310. When the absolute value of the difference between the calculated voltages $Vb_{200}$, $Vb_{400}$ is larger than the threshold S2, the switching of the frequency difference $\Delta f$ is determined to be normal at step 311.

In contrast, when the absolute value of the difference between the calculated voltages $Vb_{100}$, $Vb_{200}$ is equal to or smaller than the threshold S1, or when the absolute value of the difference between the calculated voltages $Vb_{200}$, $Vb_{400}$ is equal to or smaller than the threshold S2, the switching of the frequency difference $\Delta f$ is determined to be abnormal at step 312. Therefore, a necessary measurement is conducted at step 313.

The voltages $Vb_{100}$, $Vb_{200}$, $Vb_{400}$ corresponding to the ethanol concentration are calculated by using the frequency differences 100 kHz, 200 kHz, 400 kHz at steps 306, 307, 308, respectively. The gain is selected at step 303, 304, 305 in a manner that the voltage Vb is not saturated if the voltage Vb is calculated by using the largest frequency difference $\Delta f=400$ kHz. Thus, the voltage Vb is in the dynamic range corresponding to the detection range. Therefore, the voltage $Vb_{100}$, $Vb_{200}$, $Vb_{400}$ has a substantial true value.

When the switching of the frequency difference $\Delta f$ is normally performed by the microcomputer 50, the voltages $Vb_{100}$, $Vb_{200}$, $Vb_{400}$ are determined by the frequency difference 100 kHz, 200 kHz, 400 kHz. That is, a ratio of the voltages $Vb_{100}$:$Vb_{200}$:$Vb_{400}$ is approximately equal to a ratio of the frequency differences 100 kHz:200 kHz:400 kHz. In contrast, when the switching of the frequency difference $\Delta f$ has abnormality, the ratio of the voltages $Vb_{100}$:$Vb_{200}$:$Vb_{400}$ is different from the ratio of the frequency differences 100 kHz:200 kHz:400 kHz.

The voltage $Vb_{100}$, $Vb_{200}$, $Vb_{400}$ corresponds to a calibration voltage. For example, in a case that the ratio of the frequency differences is approximately equal to 1:2:4, when the ratio of the frequency differences is approximately equal to 1:2:3, a setting of the frequency difference may be determined to be abnormal. Further, when the ratio of the frequency differences is approximately equal to 1:1:4, a switching of the frequency difference may be determined to be abnormal.

Therefore, when the absolute value of the difference between the calculated voltages $Vb_{100}$, $Vb_{200}$ is approximately equal to the threshold S1 set based on the frequency differences 100 kHz, 200 kHz, and when the absolute value of the difference between the calculated voltages $Vb_{200}$, $Vb_{400}$ is approximately equal to the threshold S2 set based on the frequency differences 200 kHz, 400 kHz, the switching of the frequency difference $\Delta f$ can be determined to be normal.

According to the fifth embodiment, when a variation of the voltage Vb corresponding to a variation of the ethanol concentration is small (0<Vb<P), a variation of the voltage $V_{50}$ is increased by increasing the frequency difference $\Delta f$, so as to raise the solution. Thus, accurate calculation of the ethanol concentration can be possible. Further, the switching of the frequency difference $\Delta f$ can be determined to be normal or not.

(Sixth Embodiment)

An ethanol concentration sensor 1 has a determining portion to determine a switching of standard voltage to be normally performed or not, in a sixth embodiment.

A microcomputer 50 of the sensor 1 switches a standard voltage E applied to a switched capacitor circuit 20 in accordance with a voltage Vb corresponding to a detection signal of ethanol concentration, so as to improve detection accuracy. In the third embodiment, the standard voltage E is selected among three values E1, E2, E3 (E1>E2>E3). In the sixth embodiment, the ethanol sensor 1 further includes the determining portion to determine the standard voltage E to be normally set and switched.

A determination process will be described with reference to FIG. 16. The determination process is performed based on a program stored in the microcomputer 50.

The determination process is performed at the same frequency as a detection process of ethanol concentration. For example, the determination process and the detection process are alternately performed. The detection process is similar to that of the third embodiment.

When an ignition switch IG is turned on, the determination process is started to determine the setting and the switching of the standard voltage E to be normal or not. At this time, the microcomputer 50 performs an initialization at step 400.

The microcomputer 50 calculates a voltage $Vb_{E3}$ by using the smallest standard voltage E3 and the voltage Vb corresponding to the ethanol concentration at step 401. The standard voltage E is set to be the smallest value E3 among the three selectable values E1, E2, E3.

The voltage $Vb_{E3}$ is compared with thresholds $\in$, $\phi$ at step 402. As shown in FIG. 17, when the voltage $Vb_{E3}$ is larger than zero, and when the voltage $Vb_{E3}$ is equal to or smaller than the threshold $\in (0<Vb_{E3} \leq \in)$, the voltage $Vb_{E3}$ is determined to be in an area I. When the voltage $Vb_{E3}$ is larger than the threshold $\in$, and when the voltage $Vb_{E3}$ is equal to or smaller than the threshold $\phi (0<Vb_{E3} \leq \phi)$, the voltage $Vb_{E3}$ is determined to be in an area II. When the voltage $Vb_{E3}$ is larger than the threshold $\phi (\phi<Vb_{E3})$, the voltage $Vb_{E3}$ is determined to be in an area III.

When the voltage $Vb_{E3}$ is determined to be in the area I, a gain used for calculating the voltage Vb is set to have a value $\gamma$ larger than an ordinary value $\beta$ at step 403.

When the voltage $Vb_{E3}$ is determined to be in the area II, the gain used for calculating the voltage Vb is set to have the ordinary value $\beta$ at step 404.

When the voltage $Vb_{E3}$ is determined to be in the area III, the gain used for calculating the voltage Vb is set to have a value $\alpha$ smaller than the ordinary value $\beta$ at step 405.

A voltage $Vb_{E1}$ is calculated by using the standard voltage E1 and the selected gain $\gamma$, $\beta$, $\alpha$ at step 406.

A voltage $Vb_{E2}$ is calculated by using the standard voltage E2 and the selected gain $\gamma$, $\beta$, $\alpha$ at step 407.

The voltage $Vb_{E3}$ is recalculated by using the standard voltage E3 and the selected gain $\gamma$, $\beta$, $\alpha$ at step 408.

Because the smallest standard voltage E3 is used at step 401, the calculated voltage Vb is always in a dynamic range corresponding to a detection range. Therefore, the determination of the voltage $Vb_{E3}$ can be accurately performed at step 402.

Further, because the gain is selected at one of steps 403, 404, 405 based on the determination result at step 402, the voltage $Vb_{E1}$, $Vb_{E2}$, $Vb_{E3}$ calculated at step 406, 407, 408 can be made larger in the dynamic range. Therefore, accurate determination can be performed.

An absolute value of a difference between the calculated voltages $Vb_{E1}$, $Vb_{E2}$ is compared with a threshold S1 at step 409.

An absolute value of a difference between the calculated voltages $Vb_{E2}$, $Vb_{E3}$ is compared with a threshold S2 at step 410.

When the absolute value of the difference between the calculated voltages $Vb_{E1}$, $Vb_{E2}$ is larger than the threshold S1, the absolute value of the difference between the calculated voltages $Vb_{E2}$, $Vb_{E3}$ is compared with the threshold S2 at step 410. When the absolute value of the difference between the calculated voltages $Vb_{E2}$, $Vb_{E3}$ is larger than the threshold S2, the setting and the switching of the standard voltage E is determined to be normal at step 411.

In contrast, when the absolute value of the difference between the calculated voltages $Vb_{E1}$, $Vb_{E2}$ is equal to or smaller than the threshold S1, or when the absolute value of the difference between the calculated voltages $Vb_{E2}$, $Vb_{E3}$ is equal to or smaller than the threshold S2, the setting or the switching of the standard voltage E is determined to be abnormal at step 412. Therefore, a necessary measurement is conducted at step 413.

The voltages $Vb_{E1}$, $Vb_{E2}$, $Vb_{E3}$ are calculated by using the standard voltages E1, E2, E3 at steps 406, 407, 408, respectively. The gain is selected at one of steps 403, 404, 405 in a manner that the voltage Vb is not saturated if the voltage Vb is calculated by using the largest standard voltage E1. Thus, the voltage Vb is in the dynamic range corresponding to the detection range. Therefore, the voltage $Vb_{E1}$, $Vb_{E2}$, $Vb_{E3}$ has a substantial true value.

When the setting of the standard voltage E is normally performed by the generator circuit 30, and when the switching of the standard voltage E is normally performed by the microcomputer 50, the voltages $Vb_{E1}$, $Vb_{E2}$, $Vb_{E3}$ are determined by the standard voltages E1, E2, E3. That is, a ratio of the voltages $Vb_{E1}:Vb_{E2}:Vb_{E3}$ is approximately equal to a ratio of the standard voltages E1:E2:E3. In contrast, if at least one of the setting and the switching of the standard voltage E has abnormality, the ratio of the voltages $Vb_{E1}:Vb_{E2}:Vb_{E3}$ is different from the ratio of the standard voltages E1:E2:E3.

The voltage $Vb_{E1}$, $Vb_{E2}$, $Vb_{E3}$ corresponds to a calibration voltage. For example, in a case that the ratio of the standard voltages is approximately equal to 1:2:8, when the ratio of the calibration voltages is approximately equal to 1:2:5, a setting of the standard voltages may be determined to be abnormal. Further, when the ratio of the calibration voltages is approximately equal to 1:1:8, a switching of the standard voltage may be determined to be abnormal.

Therefore, when the absolute value of the difference between the calculated voltages $Vb_{E1}$, $Vb_{E2}$ is approximately equal to the threshold S1 set based on the standard voltages E1, E2, and when the absolute value of the difference between the calculated voltages $Vb_{E2}$, $Vb_{E3}$ is approximately equal to the threshold S2 set based on the standard voltages E2, E3, the setting of the standard voltage E by the generator circuit 30 and the switching of the standard voltage E by the microcomputer 50 can be determined to be normal.

According to the sixth embodiment, when a variation of the voltage Vb corresponding to a variation of the ethanol concentration is small (0<Vb<P), a variation of the voltage $V_{50}$ is increased by increasing the standard voltage E, so as to raise the solution. Thus, accurate calculation of the ethanol concentration can be possible. Further, the setting and the switching of the standard voltage E can be determined to be normal or not.

(Seventh Embodiment)

Figure 18:
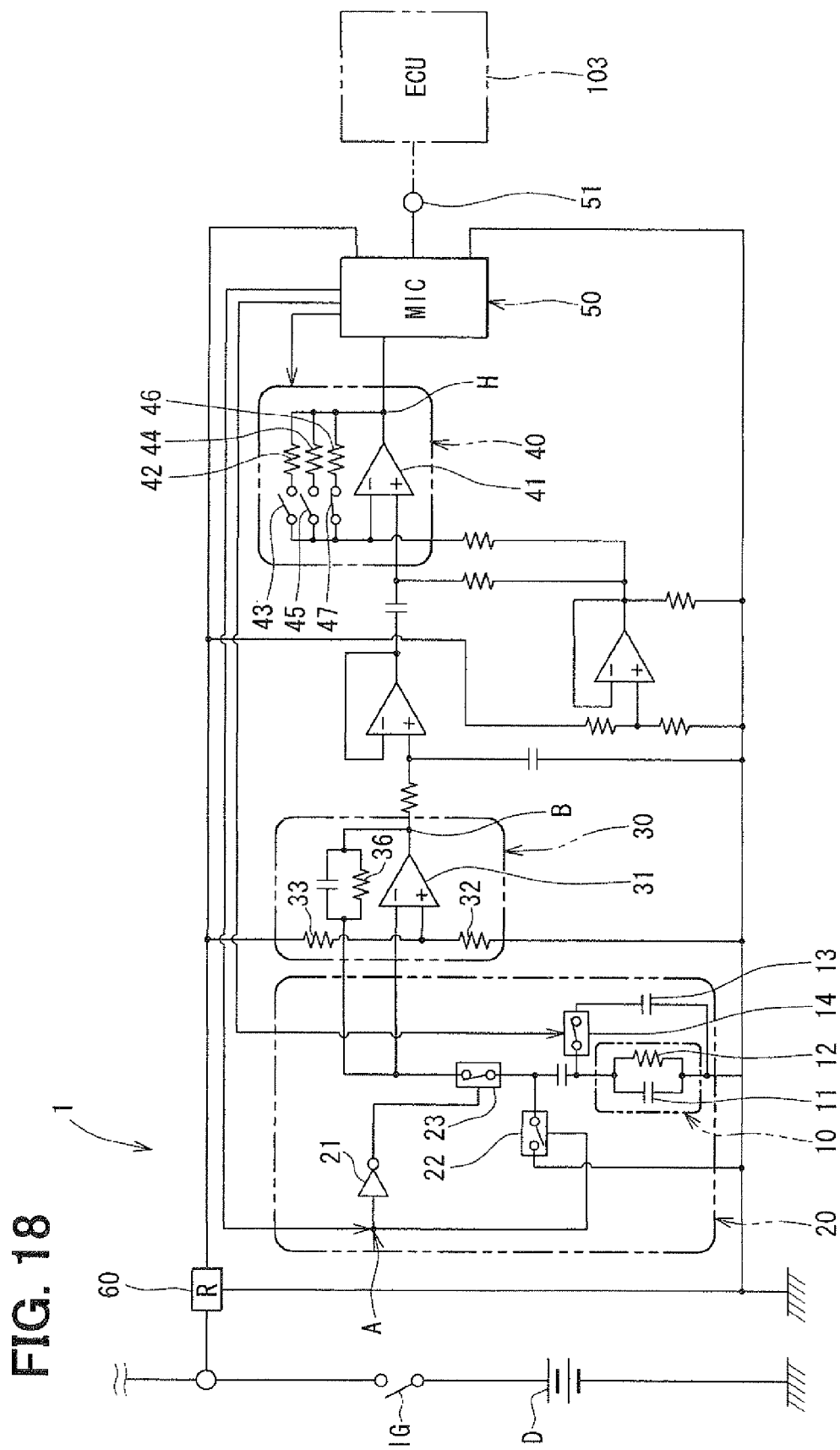
FIG. 18 is a circuit diagram illustrating a concentration sensor according to a seventh embodiment.

As shown in FIG. 18, a capacitor 13 and a switch 14 are arranged in an ethanol concentration sensor 1 of a seventh embodiment. The capacitor 13 is connected in parallel to a capacitor 11 of a capacitor part 10 of a switched capacitor circuit 20. The switch 14 switches the capacitor 13 to connect or disconnect to the capacitor part 10. A microcomputer 50 switches the switch 14 to open or close in accordance with a voltage Vb corresponding to a detection signal of ethanol concentration. FIG. 18 is a circuit diagram when the capacitor 13 and the switch 14 are arranged in the ethanol concentration sensor 1 of the first embodiment, for example.

The ethanol concentration sensor 1 of the seventh embodiment will be described.

A capacitance of the capacitor part 10 is proportionally decreased or increased relative to the ethanol concentration in fuel. When the ethanol concentration is low, the capacitance becomes small, and the voltage Vb corresponding to the detection signal of ethanol concentration becomes low.

A combined capacitance of capacitors connected in parallel with each other is equal to a sum of capacitances of the capacitors connected in parallel with each other. Therefore, when the capacitor 13 is connected to be parallel to the capacitor part 10, a capacitance of the switched capacitor circuit 20 corresponding to an ethanol concentration detector can be increased.

When the voltage Vb is low, that is when the ethanol concentration is low, the microcomputer 50 closes the switch 14 so as to connect the capacitor 13 to be parallel to the capacitor part 10. Therefore, the capacitance of the capacitor part 10 corresponding to the ethanol concentration detector is increased. Thus, a variation of the detection voltage Vb relative to a variation of the ethanol concentration is increased, thereby solution can be raised, because the detection voltage Vb and the ethanol concentration has a linear relationship. Accordingly, detection accuracy of ethanol concentration can be improved.

Because a capacitance of the capacitor 13 is known, a substantial capacitance of the capacitor part 10 can be easily calculated based on the detection voltage Vb and the capacitance of the capacitor 13. Therefore, the ethanol concentration can be accurately detected, even when the ethanol concentration is in a low range.

The detection voltage Vb is increased as the ethanol concentration is increased. The microcomputer 50 changes the switch 14 to open so as to disconnect the capacitor 13 to the capacitor part 10, when the detection voltage Vb is increased to a predetermined value. For example, the predetermined value is 80% value of the dynamic range corresponding to the detection range.

The microcomputer 50 calculates the ethanol concentration based on the capacitance of the capacitor part 10 without the capacitor 13. Because the capacitance of the capacitor part 10 becomes large, the ethanol concentration can be accurately detected.

According to the seventh embodiment, the ethanol concentration can be accurately detected, even if the ethanol concentration is relatively low.

The liquid property detecting device is described as the ethanol concentration sensor 1 in the above embodiments. Alternatively, the liquid property detecting device may be other concentration sensor for detecting other liquid component such as methanol. In this case, concentration can be accurately detected.

Such changes and modifications are to be understood as being within the scope of the present invention as defined by the appended claims.

What is claimed is:

1. A liquid property detecting device comprising:
   an electrode portion that defines a first capacitor having liquid as a dielectric material; and
   a circuit portion that calculates a concentration of the liquid, the circuit portion including:
   a generator to generate standard voltage applied to the electrode;
   a switch portion to switch the electrode to charge with the standard voltage or discharge through a grounding;
   an operation signal output portion to output
      a first operation signal having a first frequency to the switch portion so as to perform the switching in a first switch period, or
      a second operation signal having a second frequency to the switch portion so as to perform the switching in a second switch period; and
   a signal process portion to process a detection signal corresponding to a voltage of the electrode when the standard voltage is applied to the electrode, wherein
   the signal process portion calculates liquid property based on
   a first detection signal corresponding to the detection signal when the switch portion performs the switching in the first switch period, and
   a second detection signal corresponding to the detection signal when the switch portion performs the switching in the second switch period,
   the signal process portion has a gain relative to the detection signal in the calculation of the liquid property,
   the signal process portion changes the gain in accordance with at least one of the first detection signal and the second detection signal,
   the gain is configured to be increased as at least one of the first detection signal and the second detection signal is decreased, and
   the circuit portion calculates the concentration of the liquid based on the first detection signal and the second detection signal as the liquid property.

2. The liquid property detecting device according to claim 1, further comprising:
   a calibration portion to set a calibration frequency difference between the first frequency and the second frequency; and
   a determining portion to determine the change of the gain to be normal or not, wherein
   the signal process portion outputs an output voltage corresponding to the liquid concentration,
   the gain is one of a plurality of gains,
   the calibration frequency difference is set in a manner that the output voltage disables to be saturated when the calculation is performed by using each of the plurality of gains,
   the output voltage is calculated relative to each of the plurality of gains by using the set calibration frequency difference, and
   the determining portion determines the change of the gain to be normal or not based on the output voltages corresponding to the plurality of gains.

3. The liquid property detecting device according to claim 1, further comprising:
   a second capacitor connected to be parallel with the electrode; and
   a switch to switch the second capacitor to be disconnected to the electrode.

* * * * *